(12) United States Patent
Altarac et al.

(10) Patent No.: US 9,649,138 B2
(45) Date of Patent: May 16, 2017

(54) FACET SCREW AND METHOD FOR SPINAL STABILIZATION

(71) Applicant: Neurostructures, Inc., Irvine, CA (US)

(72) Inventors: Moti Altarac, Irvine, CA (US); Joey Reglos, Lake Forest, CA (US); John Fredrick Stephani, Soquel, CA (US)

(73) Assignee: NeuroStructures, Inc., Irvine, CA (US)

( * ) Notice: Subject to any disclaimer, the term of this patent is extended or adjusted under 35 U.S.C. 154(b) by 0 days.

(21) Appl. No.: 15/004,346

(22) Filed: Jan. 22, 2016

(65) Prior Publication Data

US 2016/0135852 A1    May 19, 2016

Related U.S. Application Data

(62) Division of application No. 13/403,098, filed on Feb. 23, 2012, now abandoned.

(51) Int. Cl.
| | | |
|---|---|---|
| A61B 17/56 | (2006.01) | |
| A61B 17/70 | (2006.01) | |
| A61B 17/88 | (2006.01) | |
| A61B 17/86 | (2006.01) | |
| A61B 17/17 | (2006.01) | |
| A61B 17/84 | (2006.01) | |

(52) U.S. Cl.
CPC ...... *A61B 17/7064* (2013.01); *A61B 17/1796* (2013.01); *A61B 17/864* (2013.01); *A61B 17/8635* (2013.01); *A61B 17/8877* (2013.01); *A61B 17/8891* (2013.01); *A61B 17/1757* (2013.01); *A61B 17/848* (2013.01); *A61B 17/861* (2013.01); *A61B 2017/564* (2013.01)

(58) Field of Classification Search
CPC .............. A61B 17/7064; A61B 17/864; A61B 2017/564; A61B 17/1757
USPC .................................................. 606/247–249
See application file for complete search history.

(56) References Cited

U.S. PATENT DOCUMENTS

| 7,824,429 | B2 * | 11/2010 | Culbert | .............. | A61B 17/7064 |
|---|---|---|---|---|---|
| | | | | | 606/279 |
| 8,114,158 | B2 * | 2/2012 | Carl | .................... | A61B 17/7064 |
| | | | | | 606/247 |
| 8,986,355 | B2 * | 3/2015 | Angert | ............... | A61B 17/1757 |
| | | | | | 606/300 |
| 2006/0036323 | A1 * | 2/2006 | Carl | ....................... | A61F 2/4405 |
| | | | | | 623/17.11 |

(Continued)

*Primary Examiner* — Mary Hoffman
(74) *Attorney, Agent, or Firm* — Rimas Lukas

(57) ABSTRACT

A spinal facet bone screw and minimally invasive surgical method of implanting a facet screw to stabilize the spine are provided. The facet screw includes an elongated body portion having a head, a threaded portion and a distal threadless portion. A pair of flutes formed in the elongated body extends from the distal end across the threadless portion and into the distal end of the threaded portion. The flute creates a self-tapping cutting surface that includes a heel edge that is curved with respect to the outer surface. The method of implantation comprises making a minimally invasive incision on the side of the midline contralateral to the target facet joint and delivering the screw across the interspinous process using the adjacent spinous processes as guideposts. The facet screw system fixes juxtaposed facet articular processes to enhance spinal fusion and stability and the method provides for accurate, repeatable and easy implantation.

11 Claims, 12 Drawing Sheets

(56) References Cited

U.S. PATENT DOCUMENTS

| | | | |
|---|---|---|---|
| 2007/0233093 A1* | 10/2007 | Falahee | A61B 17/683 606/86 A |
| 2009/0192551 A1* | 7/2009 | Cianfrani | A61B 17/686 606/301 |
| 2011/0313466 A1* | 12/2011 | Butler | A61B 17/7064 606/279 |
| 2013/0226239 A1* | 8/2013 | Altarac | A61B 17/7064 606/247 |

* cited by examiner

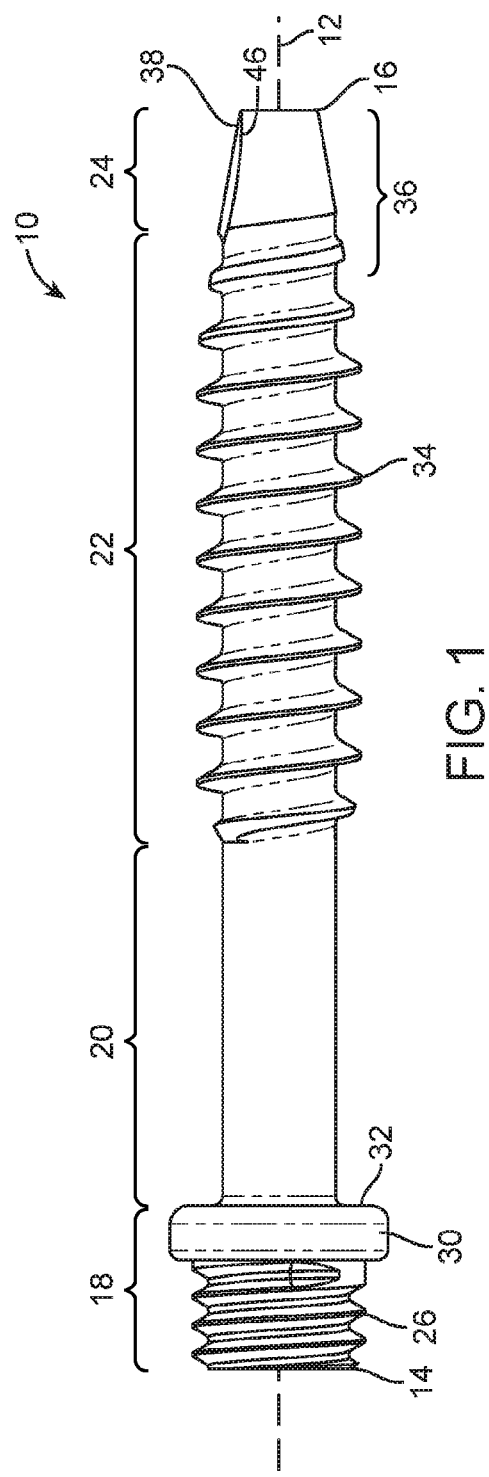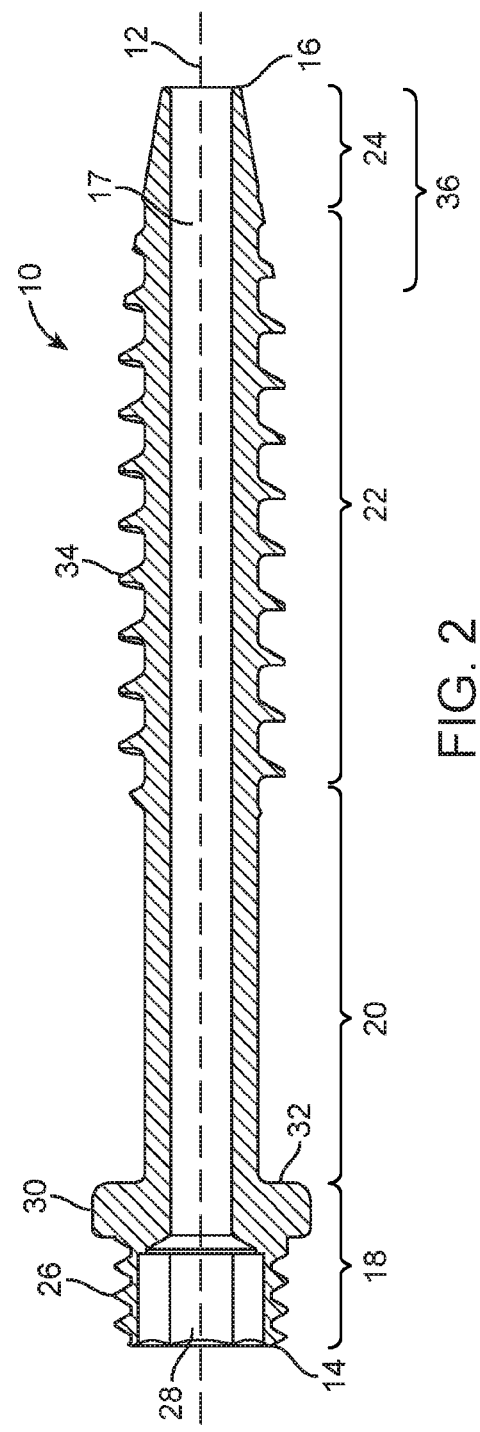

FACET SCREW AND METHOD FOR SPINAL STABILIZATION

CROSS-REFERENCE TO RELATED APPLICATIONS

This application is a divisional of co-pending U.S. application Ser. No. 13/403,098 filed on Feb. 23, 2012 entitled "Facet screw and method for spinal stabilization" and incorporated herein by reference in its entirety.

FIELD

This invention relates to spinal implants and, more particularly, to a bone screws for placement across a facet joint of the spine.

BACKGROUND

In many instances, damage to the spine as a result of advancing age, disease and injury is treated by fixation or stabilization of vertebrae. Conventional methods of spinal fixation utilize spinal fusion, a procedure in which bone growth is encouraged to bridge the disc space to fuse together adjacent vertebrae and as a result, stabilize the spinal motion segment. Spinal fusion involves at least partial removal of a damaged intervertebral disc and the introduction of bone graft material that is typically contained in an interbody spacer which is implanted into the intervertebral disc space. Kidney bean-shaped, curved or other shaped interbody spacers or cages made of titanium or polyether ether ketone (PEEK) are employed to provide decompression and house the bone graft material. The bone graft material is usually supplemented with bone morphogenic protein, demineralized bone matrix in the form of paste or cement, stem cells or other oseoinductive biological agents which are known to enhance fusion.

There are many different types of spinal fusion procedures. One is anterior lumbar interbody fusion or "ALIF". In ALIF, the patient is placed on their back and the section of the spine to be fused is approached through the front of the patient through incisions in the abdomen. The abdominal organs are moved aside, the damaged disc space is exposed and bone graft material encaged in an interbody spacer is implanted. Another spinal fusion technique is posterior lumbar interbody fusion ("PLIF") in which the spine is approached and bone graft material is implanted through the back of a patient lying prone on a surgical table. A type of PLIF is transforaminal lumbar interbody fusion or "TLIF". TLIF is another widely used method of spinal fusion for the treatment of a variety of lumbar spinal disorders when avoidance of complex anterior approaches and diminished posterior trauma is desired. In TLIF, the spine is approached through the backside of the patient as in PLIF; however, access to the interbody space is gained through the foramina. Another surgical spinal fusion technique is extreme lateral interbody fusion, also known as XLIF, which is performed through the patient's side, avoiding the major muscles of the back. Other surgical spinal fusion techniques include direct lumbar interbody fusion ("DLIF"), lateral trans-psoas interbody fusion ("SLIF") and intertransverse lumbar interbody fusion ("ILIF").

To lower the rate of imperfect fusion, i.e. pseudoarthrosis, adjuncts to spinal fusion have been employed. Most commonly, posterior instrumentation such as pedicle screws and rods are implanted on the posterior side of the spine. Four pedicle screws are typically placed into the pedicles with two pedicle screws in each adjacent vertebra. Two rods interconnect the screws of the adjacent vertebra and span the intervertebral disc space at issue. The rods are typically secured to the head of each screw with caps that are tightened down to capture the rod between the cap and screw. Other posterior instrumentation such as plates or other interconnectors may also be employed and secured to screws implanted into the pedicles.

Generally, pedicle screw fixation requires a high degree of skill that involves locating the pedicle that is not always directly visualized or may be difficult to visualize due to aberrant anatomy. Further skill is required to deliver the pedicle screw in the appropriate location with the proper angulation and the correct trajectory. Even in straightforward anatomical situations, pedicles can have various diameters and significant variations in trajectory are possible. For these reasons, fluoroscopic imaging is typically used by many surgeons to facilitate the surgical application of pedicle screws which increases the radiation exposure to the patient and surgical team. Other complications of pedicle screw placement include duration of the procedure, significant tissue dissection and muscle retraction, scarring, misplaced screws, excess rigidity leading to adjacent level disease requiring further fusions and re-operations.

An alternative to pedicle screw fixation is facet fixation in which the facet joint is significantly immobilized. Each vertebra has a pair of articular surfaces located on the left side and a pair of articular surfaces located on the right side. Each pair includes a superior articular surface that forms a facet joint with the adjacent higher vertebra and an inferior articular surface that forms a facet joint with the adjacent lower vertebra. Together the superior and inferior articular surfaces of adjacent vertebrae form a facet joint. Facet joints are synovial joints that are surrounded by a capsule of connective tissue with synovial fluid nourishing and lubricating the joint. The joint surfaces are coated with cartilage allowing the joints to articulate relative to one another. With adjacent intervertebral bodies fused together in a spinal fusion procedure, the fixation of the facet provides an additional supplement to spinal fusion. Facet fixation can also be employed as a stand alone procedure or primary means to stabilize the spine without fusion of intervertebral bodies. Facet fixation can also serve to augment pedicle screw fixation or other posterior instrumentation on one side of the spine.

Typically, in facet fixation, a single facet screw is inserted directly across the facet joint to fix or limit the motion of the facet joint. In one variation of facet screw fixation called translaminar facet screw fixation, screws are inserted from the base of the spinous process on the contralateral side and through the lamina to traverse the facet joint indirectly and into the pedicle of the successively inferior vertebra. In translaminar facet screw fixation, the translaminar facet screws are longer than the screws used in direct facet fixation. To fixate both facet joints of a motion segment, two translaminar facet screws are placed in crisscross fashion across the lamina. Other procedures involve positioning an implant in the facet joint between the articular faces which may require removal of bone and the implantation of bone graft and/or growth material with or without a facet screw across the joint. Where the lamina is weak, translaminar facet screws can toggle and even break the lamina and destabilize the joint. However, facet screw fixation offers significant advantages when compared to pedicle screw fixation. For example, bilateral facet fixation uses only two screws per level replacing four screws, two rods and associated caps used in pedicle screw fixation. Facet fixation requires less hardware, less operating time and is easier to implant. Furthermore, facet screw strength and stability is comparable to traditional pedicle screws. Facet screws also offer the potential reduction in fluoroscopic imaging resulting in less exposure to radiation due to less hardware to implant. Furthermore, facet fixation preserves adjacent level anatomy compared to pedicle screw fixation. Because of these and other advantages offered by facet screws, they are now being implanted on a regular basis. In order to further improve upon the use of such facet screws, an improved facet screw and a minimally invasive method for accurately and repeatedly placing facet screws across the facet joints is needed. This invention provides an improved facet screw and novel method of implantation.

SUMMARY

According to one aspect of the invention, a facet screw is provided. The facet screw includes a cannulated elongated body that extends between a proximal end and distal end and has a longitudinal axis. The facet screw includes a head portion at the proximal end that has a threaded outer surface, a socket open to the proximal end and a seating flange that extends radially outwardly. The facet screw further includes a threaded portion located distally of the head portion with threads formed in the outer surface of the elongate body. A threadless distal portion is located distally of the threaded portion and extends along the elongate body from the threaded portion to the distal end. At least one flute is formed longitudinally in the elongate body. The flute is located at the distal end and extends proximally toward the proximal end. The flute extends proximally into the threaded portion and interrupts threads at the distal end of the threaded portion. The flute has a radial cutting face intersecting with the outer surface of the elongate body at a straight cutting edge. Also part of the flute is a curved heel face that interconnects with the cutting face at one end and intersects with the outer surface at a heel edge wherein the heel edge is curved. The facet screw includes a distal tapered portion extending proximally along the elongate body from the distal end. The distal tapered portion has a diameter that decreases in the distal direction and encompasses the threadless distal portion.

According to another aspect of the invention, a surgical method for implanting a facet screw into a spine of a patient is provided. The method includes the step of identifying a target facet joint located on a first side of a midline of a patient's spine. The target facet joint comprises the inferior articular face of a first vertebral body and the superior articular face of an adjacent lower second vertebral body. The facet screw is inserted into a patient at a point of skin penetration located on a second side of the midline of the patient's spine that is opposite from the first side of the midline and cephalad of the target facet joint. The facet screw is moved subcutaneously from the point of skin penetration through an interspinous ligament located between the first vertebral body and adjacent higher third vertebral body at a point of interspinous ligament penetration. From the point of interspinous ligament penetration, the facet screw is moved to the first vertebral body at a location adjacent to the target facet joint on the first side of the midline. The facet screw is delivered into the bone of the first vertebral body at a location adjacent to the target facet joint and the facet screw is driven across the upper and lower articular faces of the target facet joint.

In another aspect of the invention, the method further includes several steps performed prior to inserting, moving, driving and delivering the facet screw. The method includes the step of inserting a target needle comprising a trocar portion and a cannula portion into a patient at a point of skin penetration. The distal end of the target needle is moved subcutaneously from the point of skin penetration through an interspinous ligament located between the first vertebral body and the adjacent higher third vertebral body creating a point of interspinous ligament penetration. The distal end of the target needle is moved to contact the first vertebral body at a location adjacent to the target facet joint. The target needle is docked into the first vertebral body at a location adjacent to the target facet joint. The trocar portion of the target needle is removed. A guide wire is inserted into the cannula portion of the target needle and docked into the first vertebral body at a location adjacent to the target facet joint. The facet screw is attached to the distal end of an insertion instrument. The facet screw and insertion instrument are passed over the guide wire to the first vertebral body.

In another aspect of the invention, a surgical method for implanting a facet screw across a target facet joint comprising a first vertebral body and a second vertebral body in a minimally invasive surgical procedure is provided. The method includes the step of delivering the facet screw through a skin incision contralateral to the target facet joint. The facet screw is passed through the interspinous ligament to a location on the first vertebral body adjacent to the target facet joint. The facet screw is driven into the first vertebral body. The spinous process of the first vertebral body and the spinous process of an adjacent higher third vertebral body are used as guideposts and the target facet joint is fixed with the facet screw.

BRIEF DESCRIPTION OF THE DRAWINGS

FIG. 1 is a side elevation view of a facet screw according to the present invention.

FIG. 2 is a cross-sectional view of a facet screw according to the present invention.

DETAILED DESCRIPTION

Figure 3:
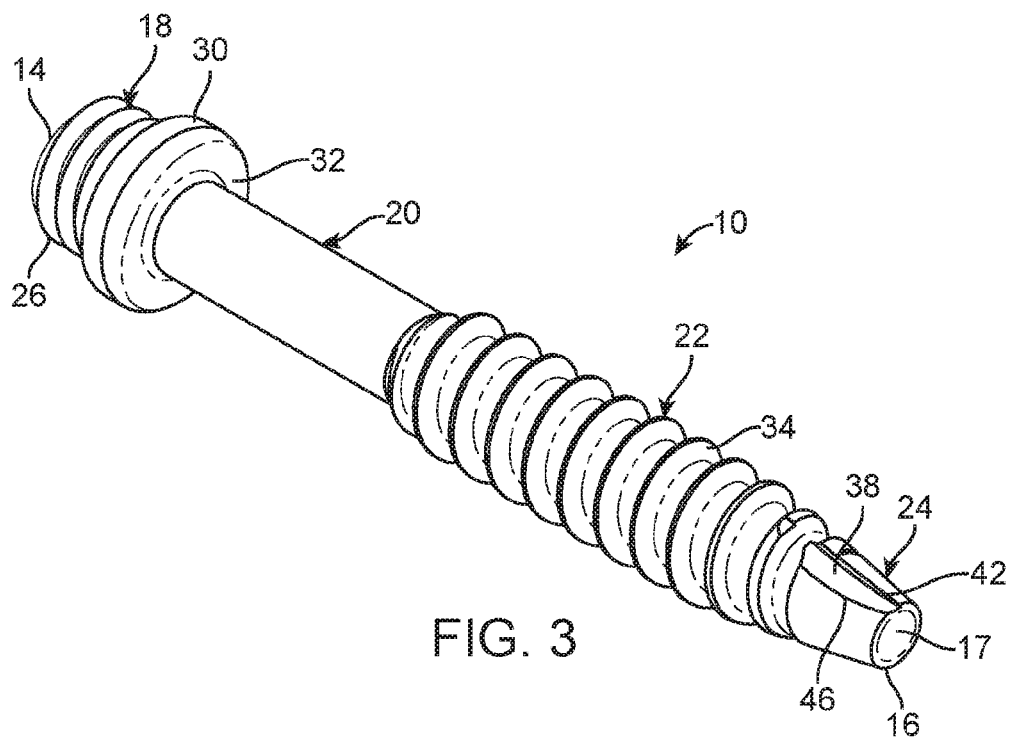
FIG. 3 is a top perspective view of a facet screw according to the present invention.

FIGS. 1-7 illustrate a spinal facet bone screw 10 according to the present invention. The bone screw 10 comprises an elongate body having an overall cylindrical shape for rotation about a longitudinal axis 12. The elongate body extends between a proximal end 14 and a distal end 16. In one variation, the bone screw 10 is cannulated having a central lumen 17 extending between the proximal end 14 and the distal end 16 for passing the bone screw 10 over a guide wire such as a Kirschner wire, commonly referred to as a K-wire. Generally, the elongate body is divided into four sections: a head portion 18, a neck portion 20, a threaded portion 22, and a threadless distal portion 24. Each section of the facet bone screw 10 and its corresponding features will now be described in detail.

Figure 6:
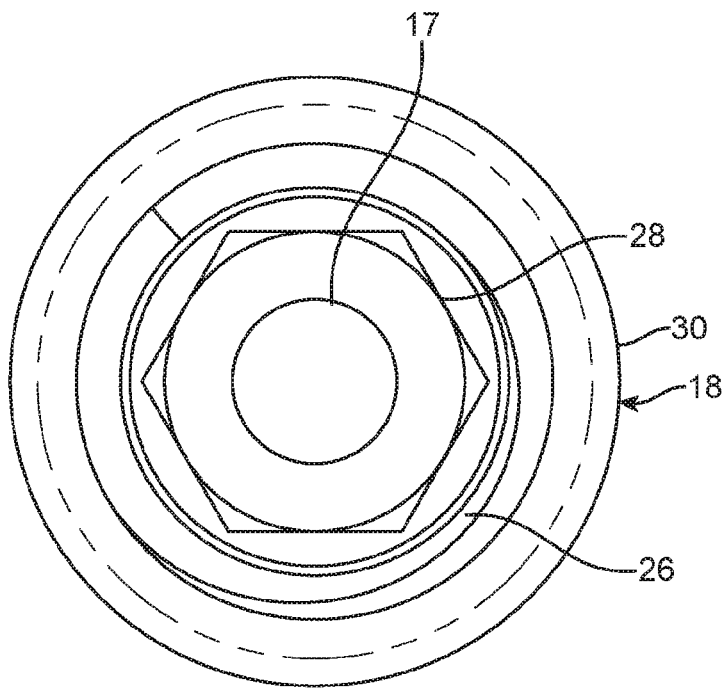
FIG. 6 is an end elevation view of a facet screw according to the present invention.
Figure 7:
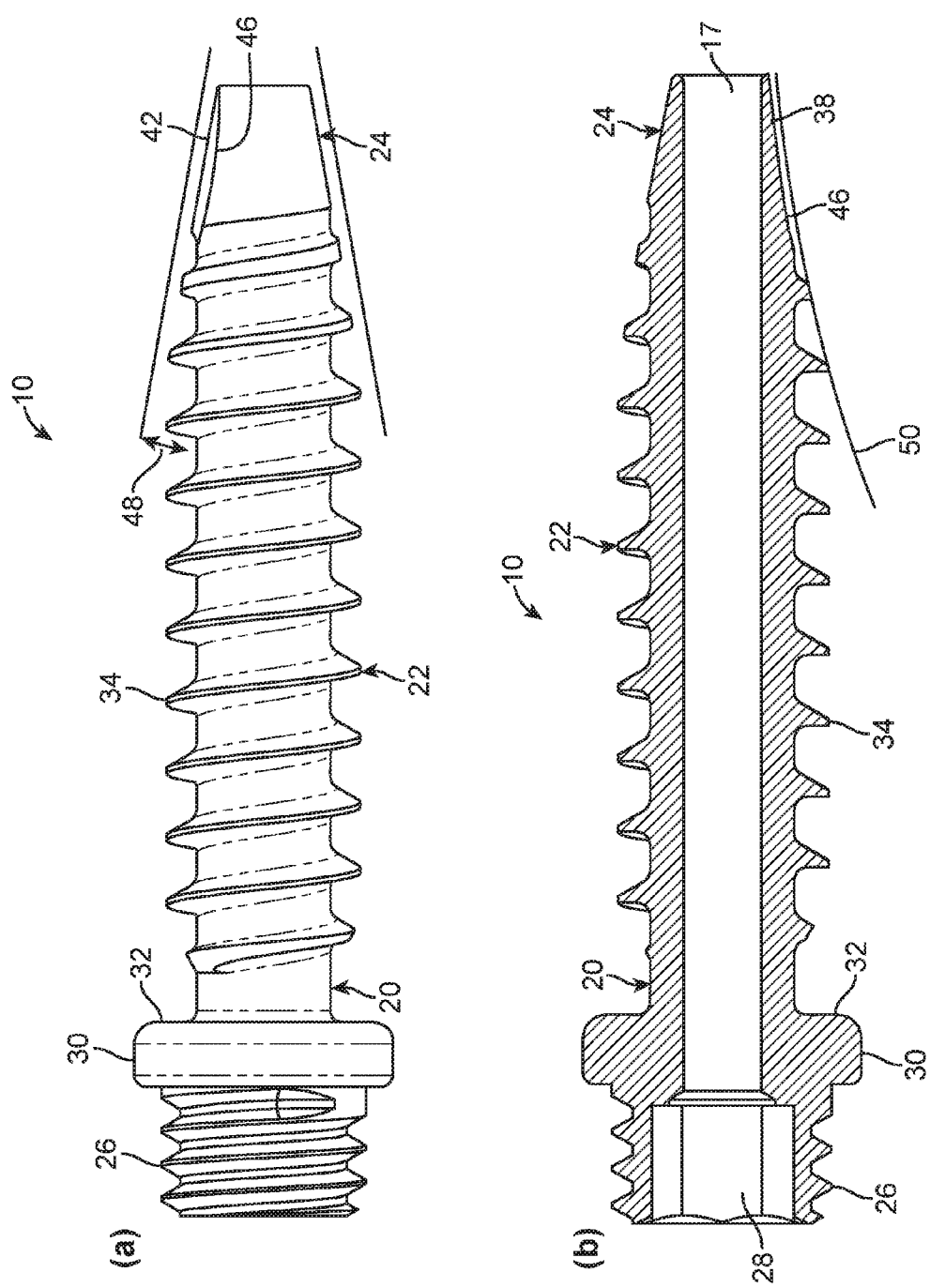
FIG. 7a is a side elevation view of a facet screw according to the present invention.
FIG. 7b is a cross-sectional view of a facet screw according to the present invention.

The head portion 18 is located toward the proximal end 14 of the bone screw 10. The head 18 defines a workable end that is adapted to be worked or gripped by a hand or power tool for rotating the bone screw 10. The head 18 has threads 26 over at least a portion of its outer surface. These threads 26 are adapted for threaded connection with inner threads of an insertion instrument or screw driver that will be described in greater detail below. The head 18 also includes a well socket 28 that is open at proximal end 14. The socket 28 is hexagonal in shape as can be seen in FIG. 6 but it can be of any suitable shape for mating with a driver. The head portion 18 further includes a circumferential seating flange 30 having a seating surface 32 facing distally at the intersection with the neck portion 20. The seating flange 30 extends radially outwardly from the neck portion 20. The seating surface 32 provides a stop against the bone and is flat to provide higher torque on seating; however, a spherical, curved or other-shaped seating surface 32 may be employed.

The neck portion 20 is located between the head portion 18 and threaded portion 22 of the elongate body. The neck portion 20 has a diameter that is less than the diameter of the seating flange 30 of the head 18. In one variation, the neck 20 is approximately a third of the overall length of the bone screw 10; whereas in the variation shown in FIGS. 4 and 7, the neck 20 is much smaller and approximately less than 10 percent of the overall length of the bone screw 10.

The threaded portion 22 is located between the neck portion 20 and the distal threadless portion 24. The threaded portion 22 includes threads 34 formed on the outer surface. The threads 34 have a major diameter larger than the diameter of the neck portion 20 and a minor diameter that is substantially the same as the diameter of the neck portion 20. The major diameter is approximately 4-7 millimeters. In a partially threaded variation as shown in FIGS. 1-3, the threaded portion 22 constitutes approximately half of the overall length of the bone screw 10. In a fully threaded variation shown in FIGS. 4 and 7, the threaded portion constitutes approximately 75 percent or more of the overall length of the bone screw 10. The threads are self-tapping and, in one variation, the threads 34 are adapted for cancellous bone.

The threadless distal portion 24 is located at the distal end 16 and does not have any threads. In one variation, there is no threadless distal portion 24 and the threaded portion 22 extends all the way to the distal end 16. The distal end 16 is flat, that is, a plane at the distal end 16 is perpendicular to the longitudinal axis 12. In another variation, the plane at distal end 16 is angled with respect to the longitudinal axis 12 and in another variation the distal end forms a sharp point. The elongate body is tapered toward the distal end 16 forming a tapered portion 36 such that the diameter of the elongate body decreases toward the distal end 16 wherein the diameter at the distal end is less than the minor diameter of the threaded portion 24. In one variation, the threadless distal portion 24 and at least a portion of the threaded portion 22 are tapered and constitute the tapered portion 36 as shown in FIGS. 1 and 2 where preferably approximately 1-3 threads are tapered. The number of tapered threads may vary. A less aggressive self-tapping bone screw has more tapered threads such as 3-5 threads of taper. Another variation has 5-8 threads of taper and in another variation, 8-10 threads of taper.

Figure 4:
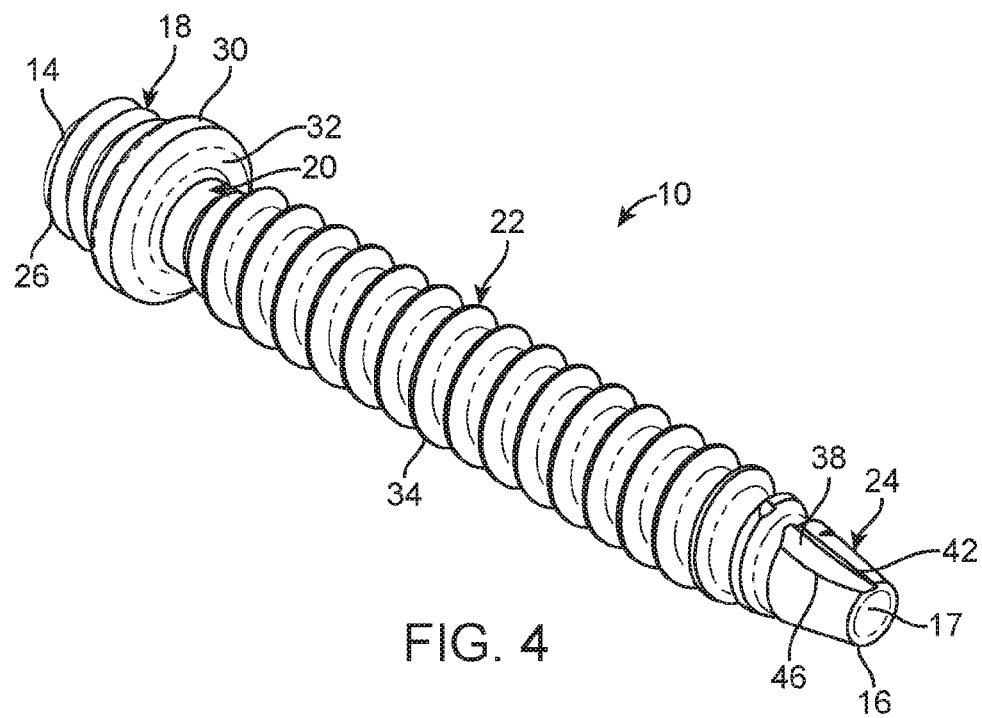
FIG. 4 is a top perspective view of a facet screw according to the present invention.
Figure 5:
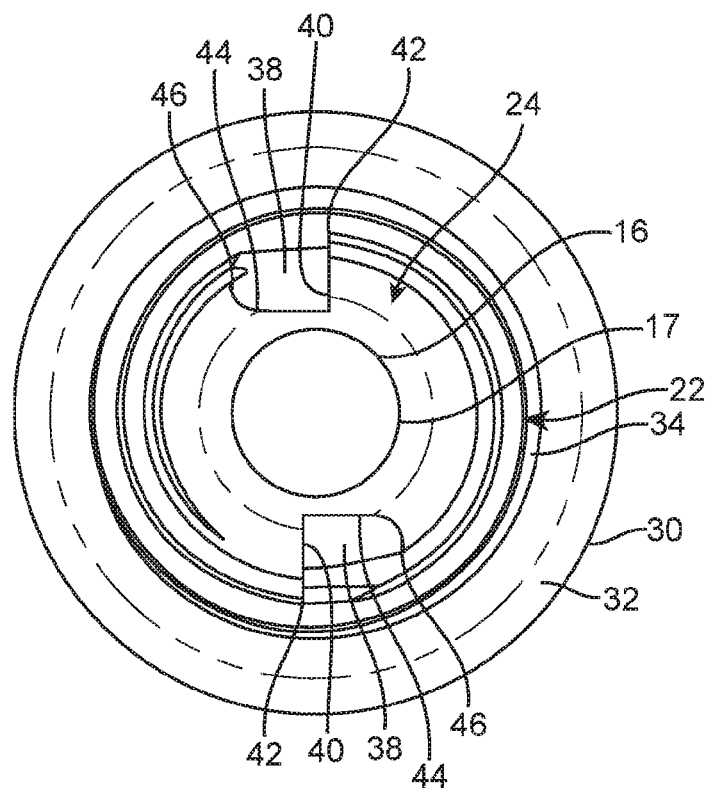
FIG. 5 is an end elevation view of a facet screw according to the present invention.

At least one flute 38 is formed in the elongate body toward the distal end 16 forming a cutting section that is approximately as long as the tapered portion 36. In another variation, the cutting section or length of the flute 38 is less than the tapered portion 36 and in yet another variation, the cutting section or length of the flute 38 is longer than the tapered portion and extends into the threaded portion 24. As can be seen in FIG. 5, two oppositely located flutes 38 are formed in the elongate body. Each flute 38 is straight and runs parallel to the longitudinal axis. The at least one longitudinally extending flute 38 is formed in the threadless portion 24 and extends from the distal end 16 into the threaded portion 22 interrupting the external threads 34. The flute 38 creates a cutting section defined by the longitudinal length of the flute 38. As can be seen in FIGS. 3 and 4, the flute 38 interrupts approximately 1 to 1.5 external threads 34 creating a gap in the continuity of the threads 34. In another variation, the flute 38 interrupts approximately 1 to 3 threads 34, in another variation, the flute 38 is even longer and interrupts approximately 3 to 5 threads 34, and in another variation, the flute 38 interrupts approximately 5 to 8 threads, and yet in another variation, the flute 38 interrupts approximately 8 to 11 threads.

With particular reference now to FIG. 5, each flute 38 includes a cutting face 40. The cutting face 40 is a radial face and, therefore, substantially parallel to a radial line. The cutting face 40 intersects with the outer surface or land of the elongated body at a cutting edge 42. Each flute 38 also includes a curved heel face 44 that intersects with the cutting face 40 at one end and intersects with the outer surface or land of the elongated body at a heel edge 46. The heel edge 46 on the cutting section is curved with respect to the outer surface as can be seen in FIGS. 1, 3, 4 and 7(b). The curved heel edge 46 provides room for ejecting bone chips. Bone chips may also travel through lumen 17 or along the threads 34 of the facet screw 10. The cutting section defined by the flute 38 allows the facet screw 10 to self tap into bone cutting threads and forming a hole without the need to pre-tap the bone. A pilot hole for self-tapping may be formed using for example, a guide wire or Jamshidi needle which will be described in greater detail below. Alternatively, the bone may also be pre-tapped with a separate tool before insertion of the facet screw 10 of the present invention but again this is not necessary.

FIG. 7(a) illustrates the taper angle 48 which is approximately 15 to 30 degrees. In another variation, the taper angle 48 is approximately 20 to 35 degrees and in another variation, the taper angle 48 is approximately 25 to 40 degrees. FIG. 7(b) illustrates the curvature 50 of the heel edge 46. The curved heel edge 46 requires less initial torque to drive the threadless portion 24 of the facet screw 10 into bone.

The facet screw 10 is made of any biocompatible material such as stainless steel, titanium, anodized titanium alloy, polymer, ceramic or other material. The facet screws 10 are provided in various sizes, such as 25, 30, 35, 40, 45 and 50 millimeter lengths, to accommodate the various anatomy of the spine.

Figure 8:
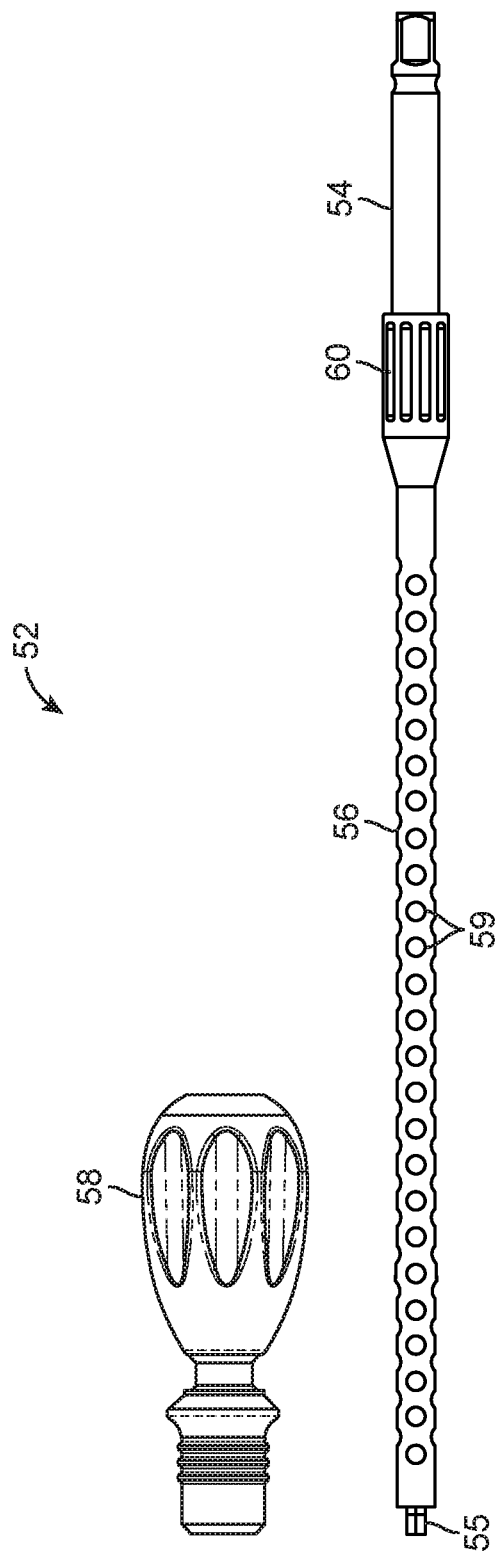
FIG. 8 is a side elevation view of an insertion instrument according to the present invention.

Turning now to FIG. 8, a facet screw insertion instrument 52 according to the present invention will now be described. The insertion instrument 52 functions to engage with, insert and deploy a facet screw 10 according to the present invention. The insertion instrument 52 releasably attaches to a facet screw 10 of the present invention to be delivered or removed from a patient. The insertion instrument 52 includes an inner shaft 54, an outer shaft 56, and a handle 58.

The inner shaft or driver 54 is substantially cylindrical in shape and includes a central bore extending from end to end that is suitable for being passed over a guide wire. The proximal end of the inner shaft 54 is releasably connectable to the handle 58 shown disconnected in FIG. 8. The handle 58 functions to rotate the inner shaft 54 in a clockwise or counter-clockwise direction for driving a facet screw 10. The distal end 55 of the inner shaft 54 is configured for mating engagement with the facet screw 10. In particular, the distal end 55 of the inner shaft 54 is hexagonally-shaped and sized to be inserted into the complimentarily-shaped, hexagonal socket 28 of the head 18. When the distal end of the inner shaft 54 is connected to the facet screw 10 and rotated at the proximal end by the handle 58, the inner shaft 54 rotates the facet screw 10 to drive it into or out of bone.

The outer shaft 56 of the insertion instrument 52 is substantially cylindrical in shape having a central bore extending from end to end. The outer shaft 56 is sized such that the inner shaft 54 fits inside the bore of the outer shaft 56. The outer shaft 56 includes a control 60 rotatably connected to the outer shaft 56. The control 60 includes a user interface such as a finger portion or grip for easily effecting rotation of the control 60 with a thumb or index finger. The outer shaft 56 is connected to the inner shaft 54 and the control 60 is configured to effect relative translation of the inner shaft 54 with respect to the outer shaft 56. The outer shaft 56 is threadingly connected to the inner shaft 54 at the control 60 such that rotation of the control 60 in one direction translates the inner shaft 54 distally relative to the outer shaft 56 and rotation of the control 60 in the opposite direction translates the inner shaft 56 proximally relative to the outer shaft 56. The distal end of the outer shaft 56 includes inner threads (not shown) formed on the inside surface of the central bore. These inner threads are configured to connect with the outer threads 26 on the head 18 of the facet screw 10. With rotation of the control 60 in one direction, the distal end of the outer shaft 56 is threaded onto the head 18 of the facet screw 10 to connect the screw 10 to the insertion instrument 52 for delivery of the screw 10 and rotation of the control 60 in the opposite direction releases the screw 10 from the insertion instrument 52 when the screw 10 is fixedly implanted into bone. Also, a plurality of apertures 59 is formed along the length of the outer shaft 56 to facilitate sterilization and removal of bone chips.

Figure 9:
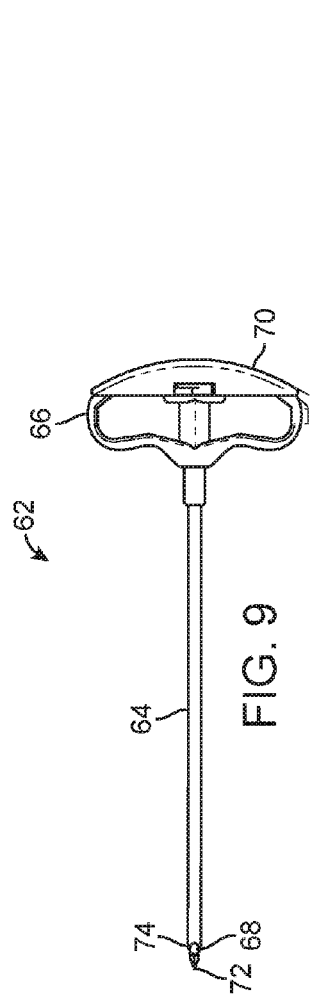
FIG. 9 is a side elevation view of a target needle.

Turning now to FIGS. 9-12, additional instruments used to implant a facet screw 10 will now be described. FIG. 9 depicts a bone biopsy needle or target needle 62 such as a Jamshidi needle. The target needle 62 includes a cannula portion 64 connected to a cannula handle 66 at the proximal end. The cannula portion 64 has a lumen that is sized and configured to receive therein a removable trocar portion 68 that has a trocar handle 70 at the proximal end. The distal end of the trocar portion 68 includes a sharp tissue and bone penetrable tip 72. The distal end of the cannula portion 64 may also include a sharp tissue and bone penetrable tip 74.

Figure 10:
FIG. 10 is side elevation view of a guide wire.

FIG. 10 illustrates a guide wire or Kirschner wire 76, commonly referred to as a "K-wire." The guide wire 76 is an elongate rod made of biocompatible material with an outer diameter of approximately 2 to 4 millimeters. The guide wire 76 has oppositely disposed distal and proximal ends 78, 80, respectively, and a cylindrical outer surface 82 extending between the ends 78, 80. The distal end 78 of each K-wire 76 includes self-tapping threads 84. The cylindrical outer surface 82 includes graduations (not shown) for measuring axial lengths along the K-wire 76.

Figure 11:
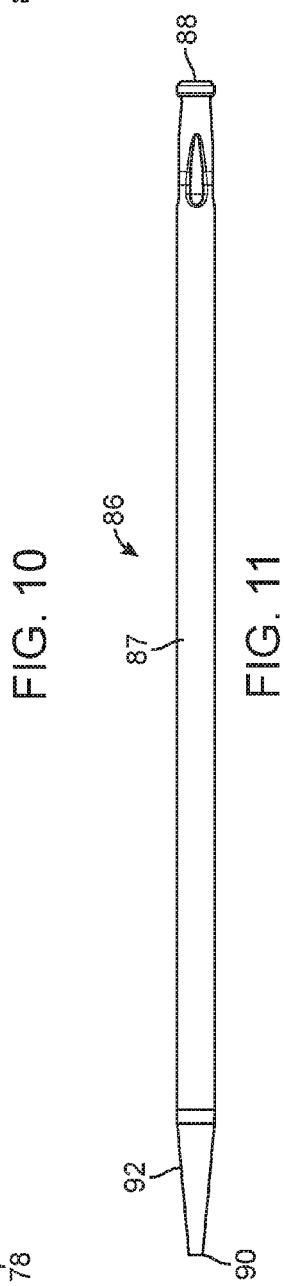
FIG. 11 is a side elevation view of a first dilator according to the present invention.
Figure 12:
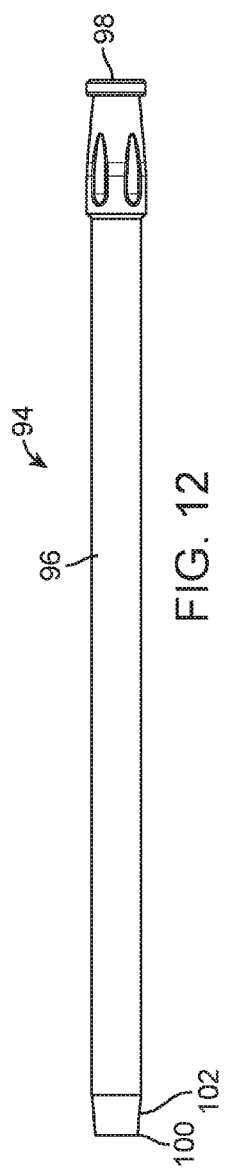
FIG. 12 is a side elevation view of a second dilator according to the present invention.

Turning now to FIGS. 11 and 12, the dilator system of the present invention includes one or more dilators configured to work independently or in conjunction with one another. When used in conjunction with one another, a first dilator 86 is generally smaller in outer diameter or cross-sectional area than that of a second dilator 94 which is also cannulated so that the second dilator 94 fits over the first dilator 86 to dilate tissue. It should be noted that the first dilator 86, in one variation, is not cannulated. In such a variation, the first dilator 86 is removed and the second dilator 94 is inserted to further open body tissue. In another variation, the first dilator 86 is cannulated to be placed over a guide wire that is first positioned in the patient and the second larger diameter dilator 94 is cannulated to fit over the first dilator 86. Although in some cases two dilators are discussed it should be noted that more than two dilators may be employed in any of the variations disclosed herein. Furthermore, some of the distal ends of the dilators of the present invention are sufficiently sharp or manufactured with integrated knife points to cut tissue without a need for a separate instrument such as a scalpel to create an initial incision in the skin or ligament which is then expanded with the dilators, whereas other dilators of the present invention have a distal end that is blunt that may or may not need a separate instrument to incise tissue.

With reference to FIG. 11 there is shown a first dilator 86. The first dilator 86 has an elongated body 87, a proximal end 88 and a distal end 90. The first dilator 86 is preferably cannulated for passage over a guide wire 76 and the elongated body 87 is substantially cylindrical in shape. The distal end 90 of the first dilator 86 has a tapered portion 92 where the diameter or cross-sectional area is less than the diameter or cross-sectional area of the body portion 87 and decreases with consecutive distal cross-sections. As shown in FIG. 11, the tapered portion 92 is substantially cone-shaped.

With reference now to FIG. 12 there is shown a second dilator 94. The second dilator 94 has an elongated body 96, a proximal end 98 and a distal end 100. The second dilator 94 includes a central lumen sized and configured for passage over the first dilator 86 to further open tissue. In one variation, the elongated body 96 is substantially cylindrical in shape. The distal end 100 of the second dilator 94 is a tapered portion 102 where the diameter or cross-sectional area is less than the diameter or cross-sectional area of the body portion 96 and decreases with consecutive distal cross-sections. As shown in FIG. 12, the tapered portion 102 is substantially cone-shaped and the length of the tapered portion 102 is shorter than the tapered portion 92 of the first dilator 86.

The spinal facet bone screw 10 is designed to fix juxtaposed facet articular processes as an adjunct to fusion to enhance spinal stability through immobilization of the facet joints. As described above in the background, there are many different types of spinal fusion procedures which the facet screw 10 of the present invention may supplement. One is called anterior lumbar interbody fusion or "ALIF". In ALIF, the patient is positioned on their back and the section of the spine to be fused is approached through the front of the patient via incisions in the abdomen. The abdominal organs are moved aside, the damaged disc space is exposed and bone graft material located in an interbody spacer is implanted. Another spinal fusion technique is posterior lumbar interbody fusion ("PLIF") in which the spine is approached and bone graft material is implanted through the back of a patient lying prone on a surgical table. A type of PLIF is transforaminal lumbar interbody fusion ("TLIF"). TLIF is another widely used method of spinal fusion for the treatment of a variety of lumbar spinal disorders when avoidance of complex anterior approaches and diminished posterior trauma is desired. In TLIF, the spine is approached through the backside of the patient as in PLIF; however, access to the interbody space is gained through the foramina. Another surgical spinal fusion technique is extreme lateral interbody fusion, also known as XLIF, which is performed through the patient's side, avoiding the major muscles of the back. Other surgical spinal fusion techniques include direct lumbar interbody fusion ("DLIF"), lateral trans-psoas interbody fusion ("SLIF"), intertransverse lumbar interbody fusion ("ILIF") and paracoccygeal approaches.

The spinal facet screw 10 of the present invention may serve as a stand alone system for posterior stabilization and thusly implanted on one or both sides of the motion segment without accompanying interbody fusion. Whether used as a stand alone system for posterior stabilization or as an adjunct to fusion, the spinal facet bone screw 10 of the present invention can be combined with other posterior stabilization instrumentation wherein the facet screw is placed on one side of the motion segment and other posterior stabilization instrumentation is placed on the other side. For example, a fusion construct can employ ipsilateral pedicle screw and rod placement on the side of TLIF and percutaneous facet screw placement on the contralateral side of the motion segment or vice versa.

The facet screw 10 is used for facet fixation at single or multiple levels from C2 in the cervical spine to S1 inclusive. The facet screw 10 of the present invention can be combined with an interfacet implant or bone graft or other bone growth inducing agents to aid fusion across the facet joint. The facet screw 10 is indicated for treatment of spondylolisthesis, pseudoarthrosis, failed previous fusion that is symptomatic, spondylolysis, degenerative disc disease as defined by neck and/or back pain of discogenic origin as confirmed by radiographic studies, degeneration of the facets with instability, trauma, dislocation and fracture.

Figure 13:
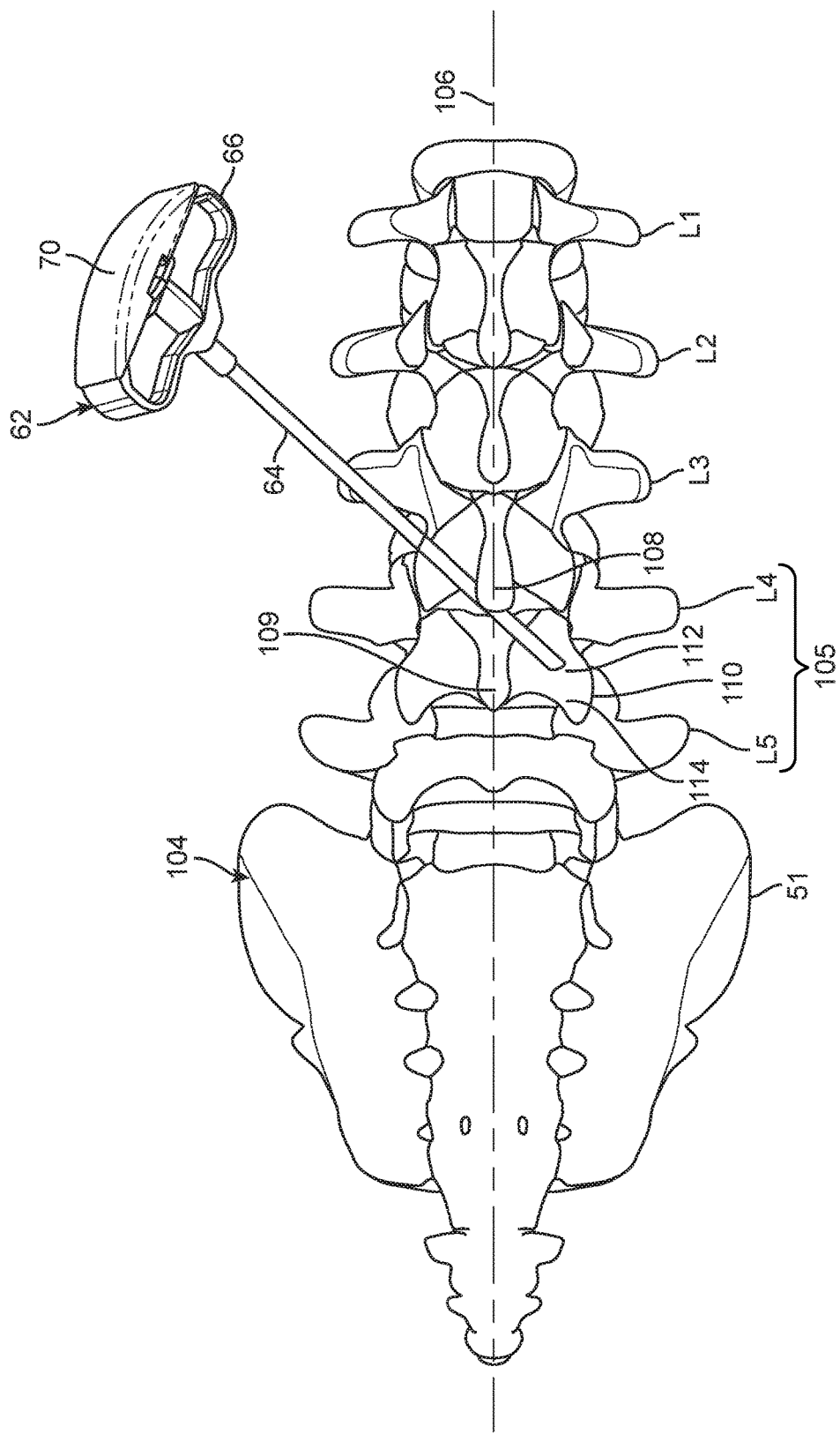
FIG. 13 is a top planar view of a target needle inserted into a portion of a spine according to the present invention.

Turning now to FIGS. 13-21, a surgical method for implantation of the facet screw 10 according to the present invention will now be described in detail. FIG. 13 illustrates a partial top view of the posterior spinal column 104 from L1 to L5 and S1 of a patient placed prone on an operating table such as a Jackson table such that the lumbar spine 104 is in anatomic lordosis. In FIG. 13, the target motion segment 105 comprises L4 and L5 for exemplary purposes only because the facet screw is not limited for implantation solely in the lumbar spine. Of course, pre-operative evaluation of the subject and particularly of the size, position, and configuration of the target vertebrae or target motion segment 105 to which the facet screw 10 is to be attached is conducted via fluoroscopy or computed tomography to determine what size facet screw 10 and trajectory will be best suited for the patient. The facet screw 10 to be used is then selected for application to the subject's vertebrae and may be further re-selected during surgery. The facet screw 10 to be applied to the subject's vertebra is initially provided to the user in the form of a kit which includes all the tools shown in FIGS. 8-12 and a group or range of different sizes of facet screws 10, one or more of which may be used for the subject during the surgery.

Prior to making an incision into a patient, a guide wire may be placed on the patient's back running parallel to the midline 106 of a patient's spine and approximately at the location of the facets and pedicles to define an interpedicular line. Anterior-posterior ("AP") fluoroscopic views are taken to confirm the interpedicular line. The guide wire may be repositioned and the interpedicular line re-confirmed as necessary. After the location is established, the interpedicular line is drawn on the skin with a marking pen.

AP and lateral fluoroscopic views are taken to locate the target facet joint 110. A second guide wire is placed obliquely and mediolaterally to intersect with the interpedicular line at the approximate location of the target facet joint 110 and to also intersect with the midline at the base of the spinous process 108 of L3, the vertebra just superior of the target motion segment 105 or between the spinous processes 108, 109. AP fluoroscopic views are taken to confirm the caudal angle from the midline. The sagittal plane at the midline between the spinous process 108 of L3 and the spinous process 109 of the superior vertebra L4 of the target motion segment 105 defines the interspinous ligament (not shown) that is also on the trajectory according the present invention, that is the interspinous ligament is traversed in this surgical method. Hence, the oblique and mediolateral trajectories crossing the midline 106 between the spinous processes 108, 109 and in one variation at the base of the spinous process 108 of L3 are marked on the skin with a pen and extend to the side opposite to the target facet joint 110. The oblique line on the skin constitutes the trajectory as projected onto the plane of the patient's skin. This planar projection of the trajectory onto the patient's skin would be in the same location shown in FIG. 13 to be along the cannula portion 64 of the target needle 62.

AP and lateral fluoroscopic views are taken to locate the starting point 112. The use of the word point is not limited to a single point but is meant to be inclusive and to define a general region, area, surface, location, approximation or collection of points. The starting point 112 of the facet screw 10 is the point or general area of entry or penetration of the screw 10 into the superior vertebra of the target motion segment 105 which is L4 in the exemplar case. This point of entry 112 into bone is approximately a point at or immediately cephalad to the most dorsal projection of the target facet joint 110. Described in another way, the starting point 112 is at or immediately cephalad of the inferior articular process 114 of the superior vertebra L4 of the motion segment 105 and just caudal of the pars interarticularis. The starting point 112 may also be described by the intersection of a plane and one line, the line being the vertical interpedicular line or the line that intersects the medial border of the same pedicle and the plane being a transverse plane that is substantially coplanar with the inferior endplate 116 (seen in FIG. 14) of the superior vertebra L4 of the target motion segment 105 or a transverse plane that includes the projection of the endplate 116 of the superior vertebra L4 of the target motion segment 105 onto a plane perpendicular to the transverse plane. The line of the endplate 116 of the superior vertebra L4 of the target motion segment 105 is readily identifiable in an AP fluoroscopic view. The starting point 112 is included on the trajectory.

The type and size of the incision into the patient is according to surgeon preference. The facet screw 10 and associated instrumentation is well adapted for conventional, open surgery, mini-open or percutaneous, minimally invasive surgical placement. Even though the bone screw can be inserted using a mini-open technique, a percutaneous approach is the preferred method with approximately a 10-20 millimeter size incision. Alternatively, a minimally invasive percutaneous stab incision, such as with a Jamshidi needle, that creates an even smaller incision of less than 10 millimeters is another preferred method that also minimizes blood loss, soft tissue disruption, scarring and recovery time.

The point of entry into the patient's skin is another region along the trajectory. The point or region of entry into the patient's skin is on the side contralateral to the target facet joint 110 and along an oblique caudal angle from the midline. In one variation, the entry point is adjacent to the spinous process 108 of the vertebral body L3 that is superior to the targeted motion segment 105 comprising L4 and L5. If lines are drawn on the patient's skin as described above, the entry point into the patient's skin will be along the oblique line shown by cannula portion 64 of the target needle 62 in FIG. 13. If the incision is taken closer to the midline along the oblique line, the incision will be larger relative to an incision that is further away from the target facet joint 110. In one variation, the incision is on the side of the spinous process 108 that is contralateral to the target facet joint 110 and in another variation at the intersection with the interpedicular line drawn on the contralateral side of the target facet joint 110.

Figure 14:
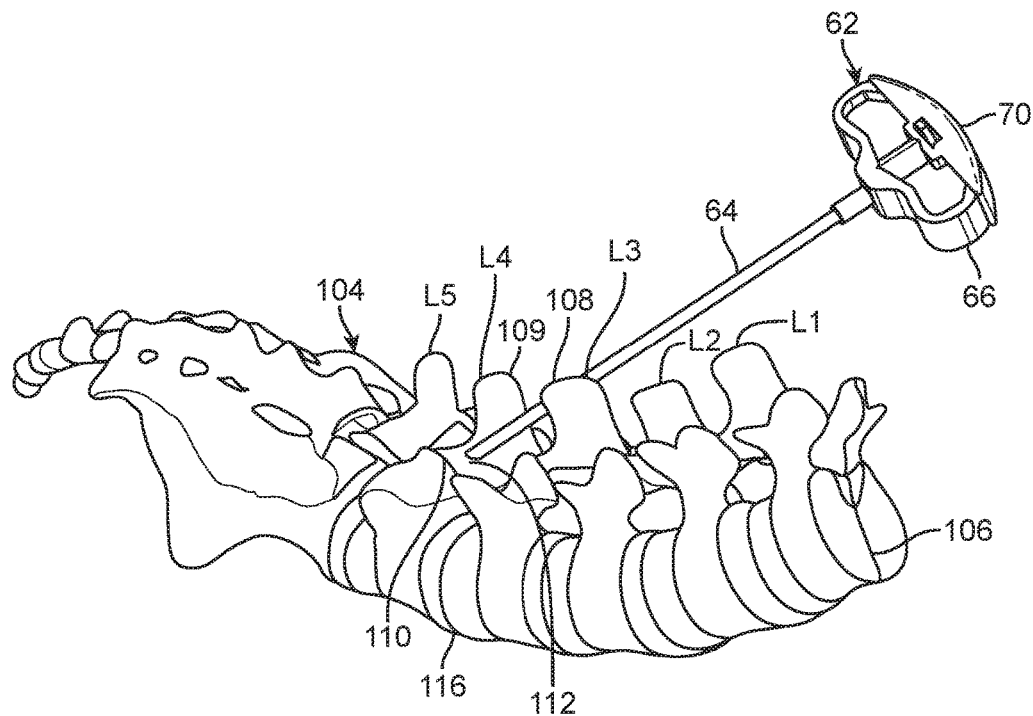
FIG. 14 is a top perspective view of a target needle inserted into a portion of a spine according to the present invention.

As shown in FIGS. 13 and 14, a target needle 62 is introduced into the patient along the expected trajectory of the facet screw under intraoperative fluoroscopy. The trajectory includes the skin entry point that is contralateral to the target facet joint 110 with the skin entry point lying along an oblique line at a caudal angle to midline. In one variation, the skin entry point will be adjacent to the spinous process 108 of the vertebral body L3 that is superior to the targeted motion segment 105 comprising L4 and L5 and in another variation it will also be in line with an interpedicular line projected onto the skin surface on the contralateral side of the target facet joint 110. The trajectory proceeds through the interspinous ligament between the spinous process 108 of the vertebral body L3 that is superior to the targeted motion segment 105 and spinous process 109 of superior vertebral body of the motion segment 105. The trajectory further proceeds into the superior vertebral body L4 of the target motion segment at the starting point 112.

The trajectory through and across the interspinous ligament from one side of the spinous processes to the other side of the spinous processes is facilitated by the spinous processes 108, 109 themselves which advantageously serve as guideposts. In one variation, the surgical method includes contacting the base of the spinous process 108 with the instrumentation including the insertion instrument 52, target needle 62, first dilator 86 and second dilator 94. In another variation, the method includes contacting the top of the spinous process 109. In yet another variation, the method includes contacting both the base of spinous process 108 and the top of spinous process 109. Such contact with one or both of the spinous processes 108, 109 advantageously directs the instrumentation to the starting point 112. In one variation, the instrument or final dilator 94 diameter is configured such that contact with both the base of spinous process 108, and the top of spinous process 109 can be made with the surface of the instrument or final dilator 94 at two locations along the length of the instrument or final dilator 94.

After contact is made with the bony portion of the vertebra with the target needle 62, the sharp trocar tip 72 may be docked into bone and fluoroscopic views taken to confirm that the contact point is at the starting point or region 112. The starting point or region 112 is cephalad to the peak of the facet in the general location of the base of the upslope. The target needle 62 is visually aligned with the pedicle such that it is at an angle to stay within the pedicle walls. After correct positioning, the sharp cannula tip 74 is docked into bone with a gentle mallet hit on the trocar handle 70 or on the cannula handle 66 with the trocar portion removed.

Figure 15:
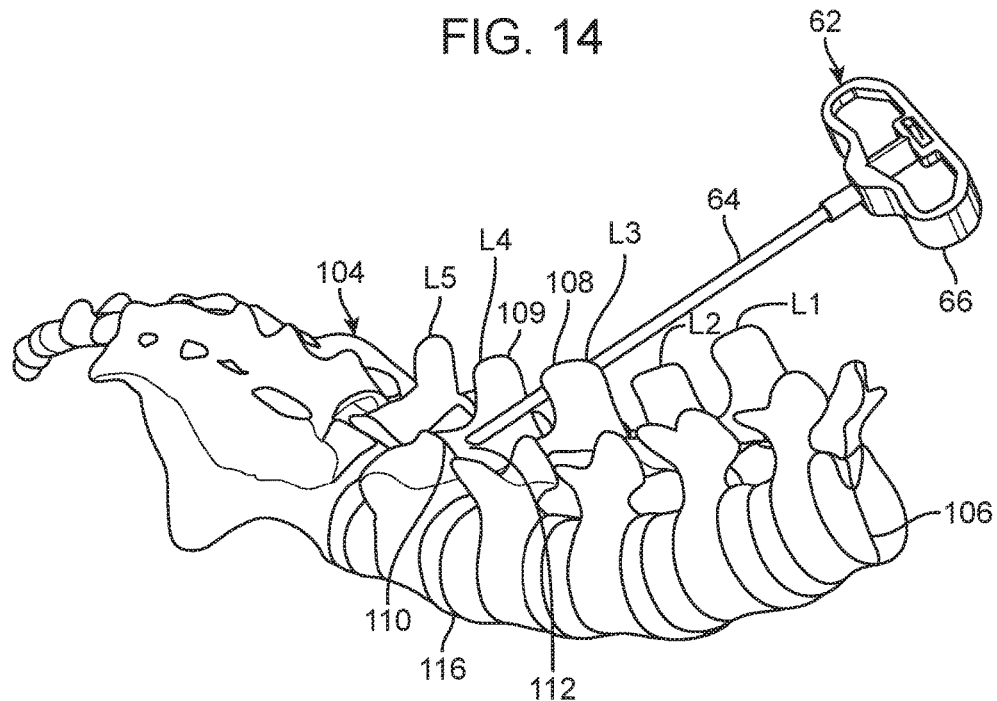
FIG. 15 is a top perspective view of a target needle with a trocar portion removed and cannula portion remaining inserted into a portion of a spine according to the present invention.

Turning now to FIG. 15, the trocar portion 68 of the target needle 62 is removed from inside the cannula portion 64 by grasping the trocar handle 70 at the proximal end and pulling it out. The cannula portion 64 and cannula handle 66 are left remaining docked in the vertebra as shown in FIG. 15.

Figure 16:
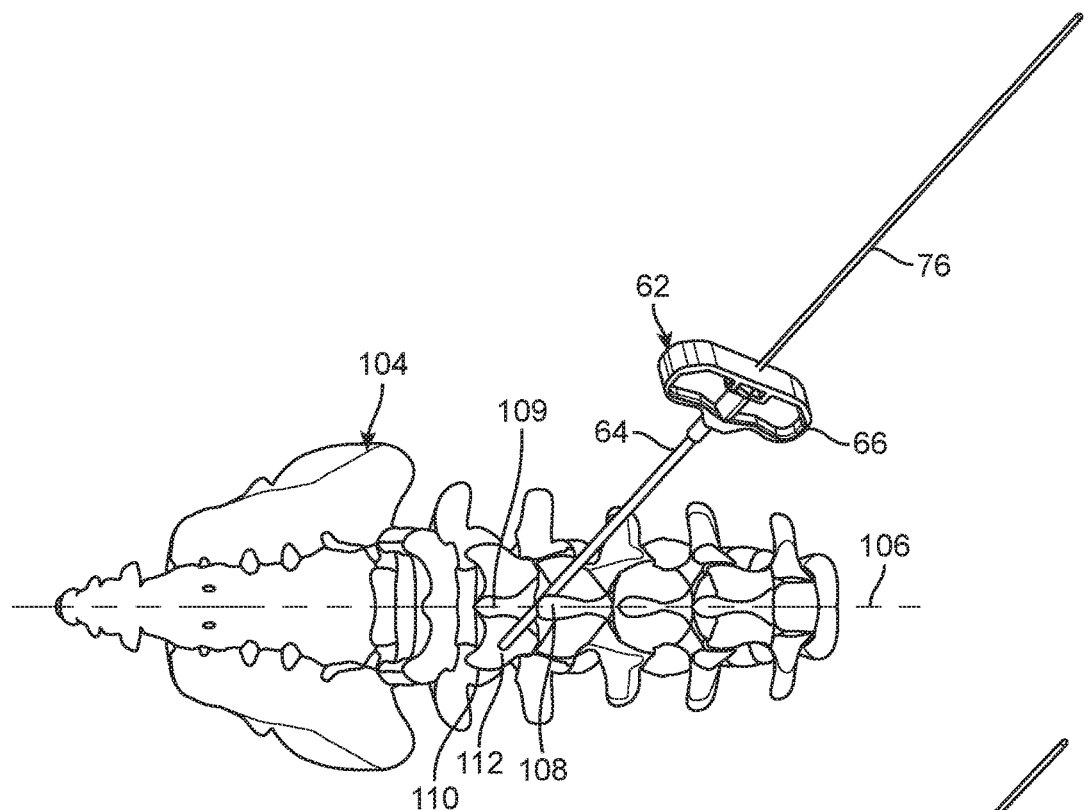
FIG. 16 is a top planar view of a guide wire inserted into a cannula portion of a target needle inserted into a portion of a spine according to the present invention.
Figure 17:
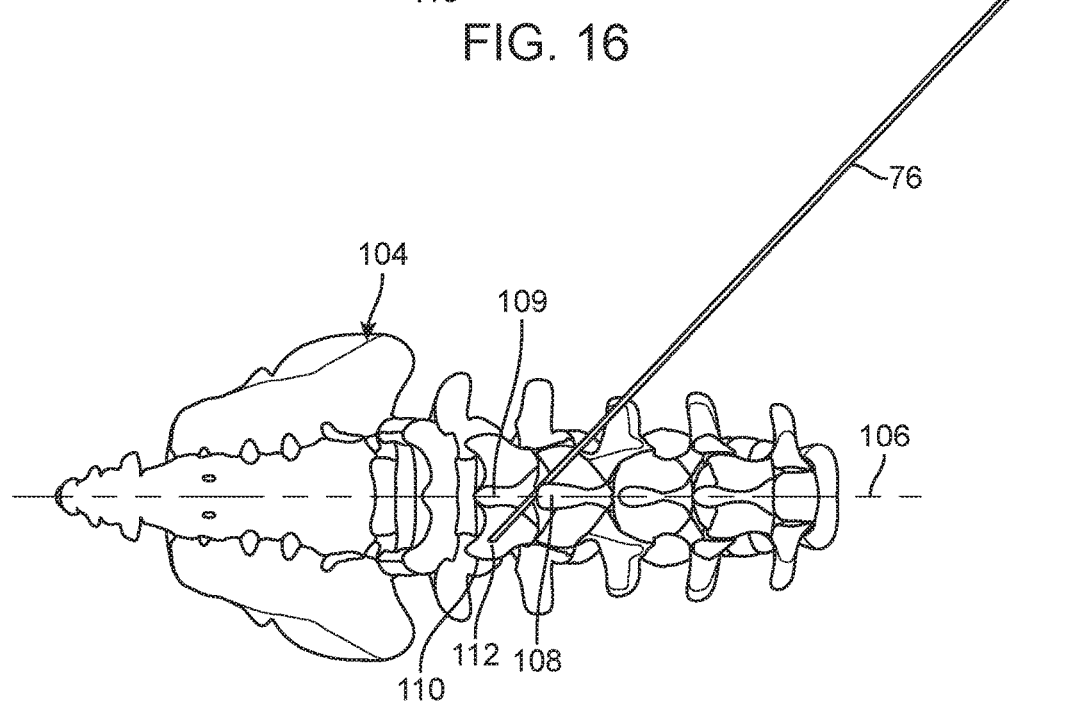
FIG. 17 is a top planar view of a guide wire inserted into a portion of a spine according to the present invention.

Turning now to FIG. 16, a guide wire 76 is inserted into the proximal end of the target needle 62 into the cannula portion 64 until the distal end 78 of the guide wire 76 contacts the starting point 112. The guide wire 76 is then drilled into bone to sink several of the guide wire threads 84. After the guide wire 76 is placed, the cannula portion 64 of the target needle 62 is removed leaving the guide wire 76 inside the patient as shown in FIG. 17.

Figure 18:
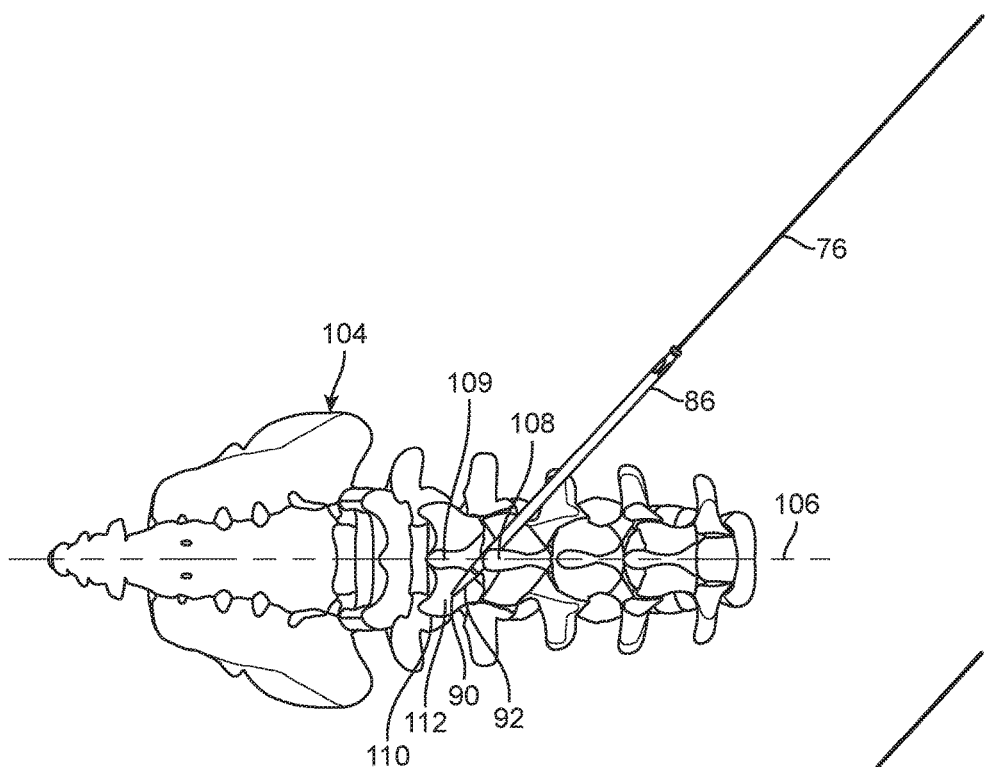
FIG. 18 is a top planar view of a first dilator delivered over a guide wire to a portion of a spine according to the present invention.
Figure 19:
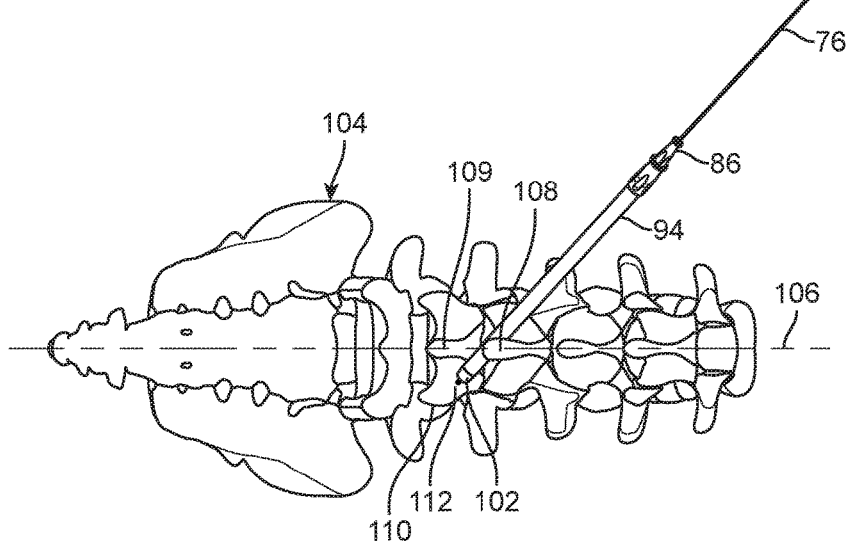
FIG. 19 is a top planar view of a second dilator delivered over a guide wire over a first dilator to a portion of a spine according to the present invention.
Figure 20:
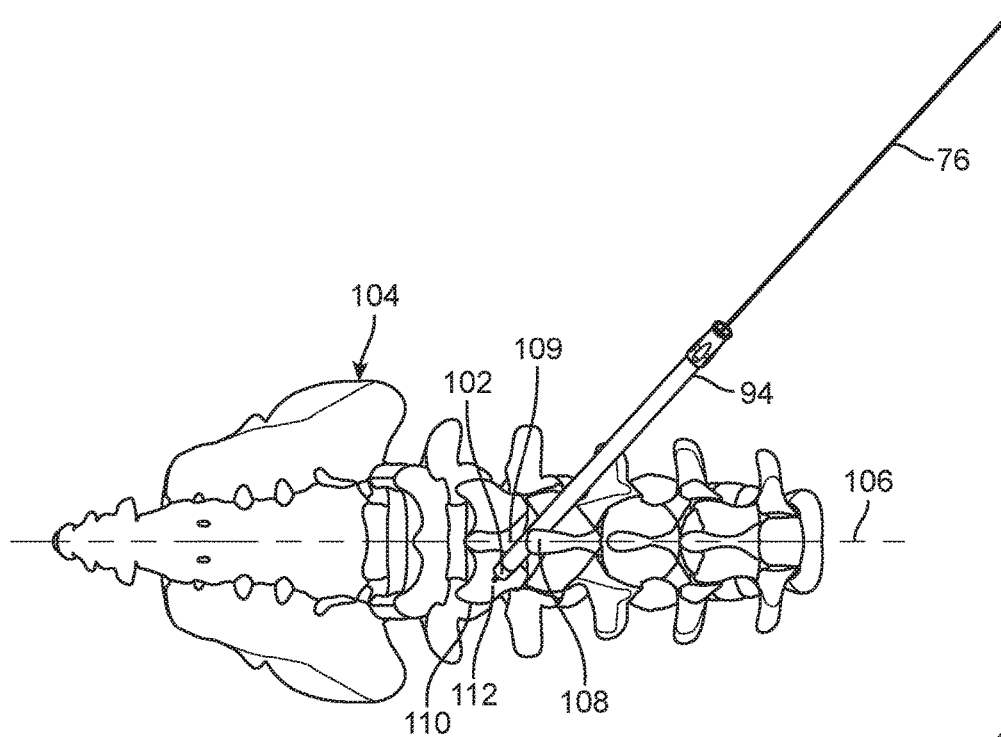
FIG. 20 is a top planar view of a second dilator delivered over a guide wire to a portion of a spine according to the present invention.

Turning now to FIG. 18, a first dilator 86 is inserted into the patient. The first dilator 86 is inserted over the guide wire 76 such that the distal end 90 leads the insertion and the guide wire 76 is inside the lumen of the first dilator 86. The tapered portion 92 of the first dilator 86 spreads apart tissue increasing the diameter of entry. The first dilator 86 is inserted until the distal end 90 contacts the vertebral bone at starting point 112. After the first dilator 86 is positioned, a second dilator 94 is delivered into the patient. The second dilator 94 is also delivered over the guide wire 76 and over the first dilator 86 such that the distal end 100 leads the insertion and the guide wire 76 and first dilator 86 are positioned inside the lumen of the second dilator 94. The second dilator 94 further spreads apart tissue increasing the diameter of entry beyond the diameter of entry created by the first dilator 86. The second dilator 94 also has a tapered portion 102 that assists in the penetration. The resulting placement of the second dilator 94 over the first dilator 86 is shown in FIG. 19. Although two dilators 86, 94 are employed in this example, tissue dilation may be accomplished with the use of only one dilator. Also, sequential dilation may proceed with more than two dilators to achieve incremental dilation up to the desired diameter opening. Alternatively, dilation with dilators 86, 94 may be avoided completely and the insertion instrument 52 with an attached facet screw 10 can be inserted directly through the soft tissue. The second or final dilator 94 may include a sharp distal end 100 such that it can be docked into the vertebral bone to keep it in position. After the second dilator 94 is docket or in position, the first dilator 86 is removed from inside the second dilator 94 by pulling it proximally out of the patient. FIG. 20 illustrates the first dilator 86 removed with the second dilator 94 remaining in position inside the patient.

Figure 21:
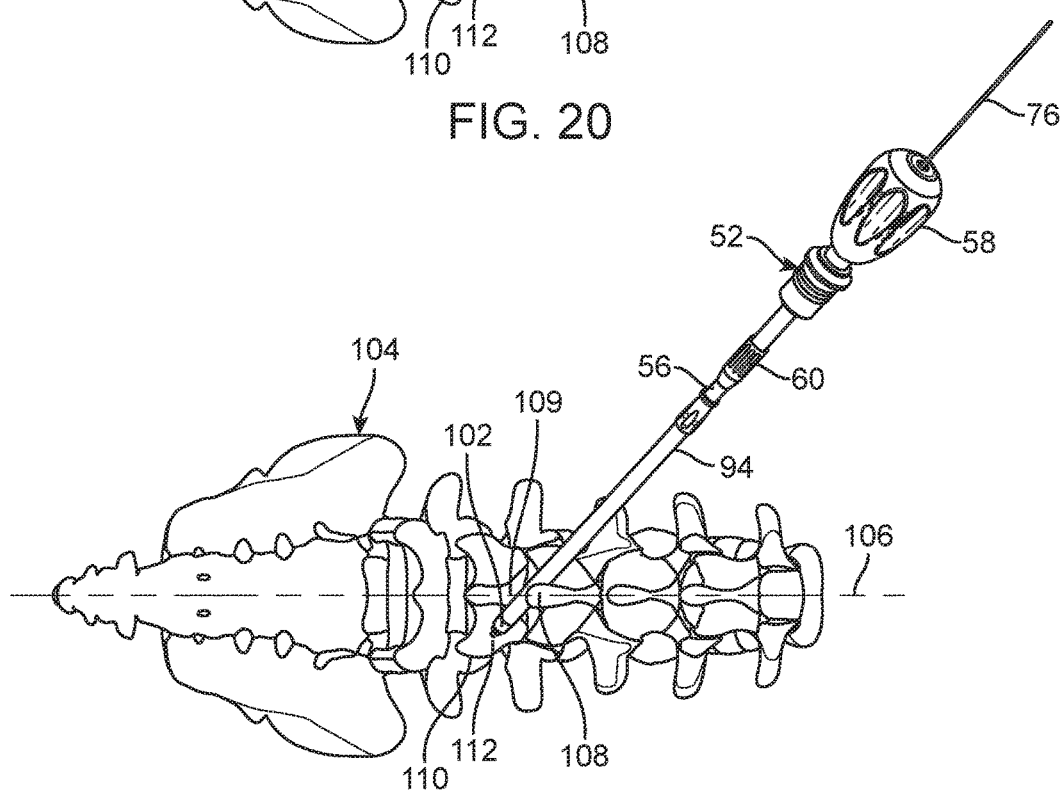
FIG. 21 is a top planar view of an insertion instrument delivered over a guide wire and into the second dilator to a portion of a spine according to the present invention.
Figure 23:
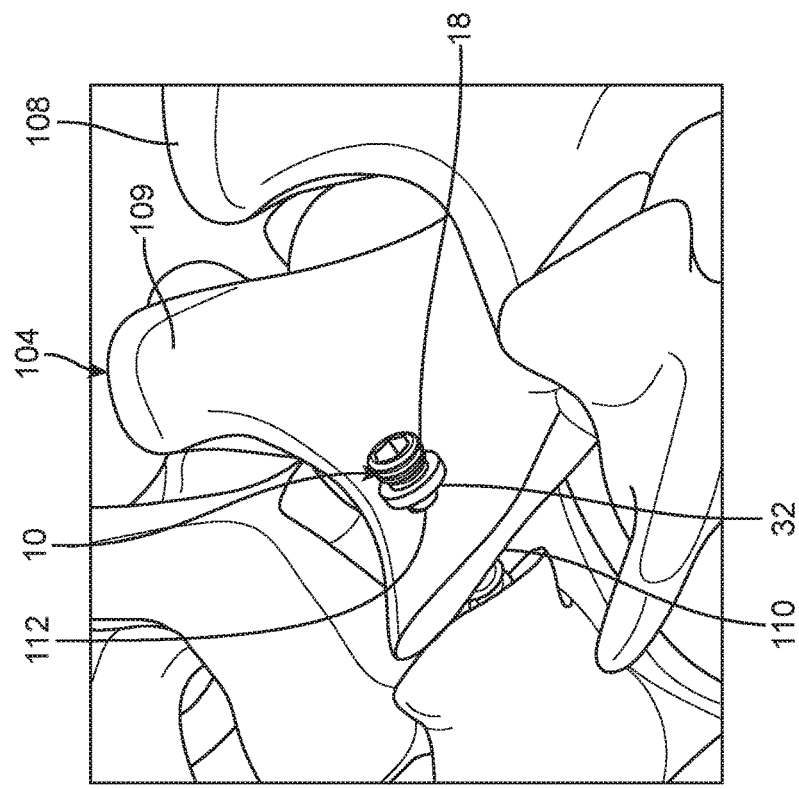
FIG. 23 is top perspective view of a facet screw implanted into a portion of a spine according to the present invention.
Figure 22:
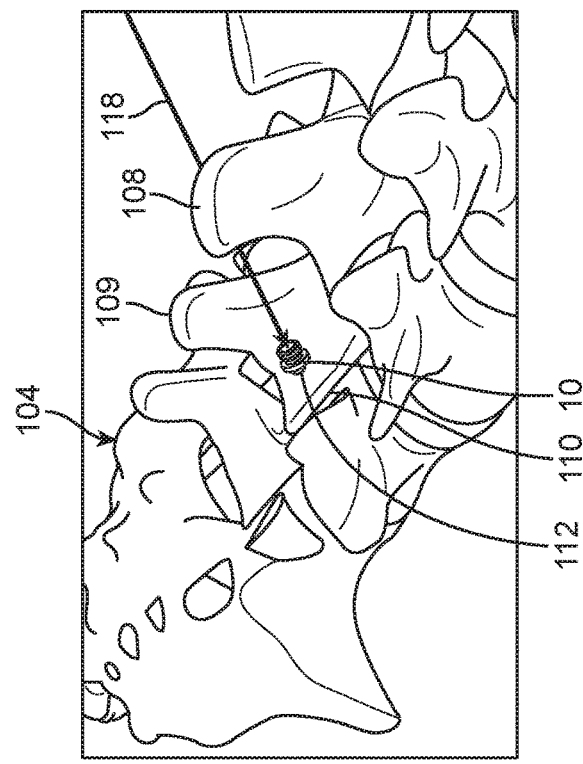
FIG. 22 is a top perspective view of a facet screw implanted into a portion of a spine according to the present invention.

In one variation, or by surgeon preference, the screw hole is now ready to be prepared by inserting a tap into the second dilator 94 to tap or create a pilot hole in the vertebral bone. However, such preparation is not necessary with the self-tapping facet screw 10 of the present invention. The selected facet screw 10 is loaded onto the insertion instrument 52. The distal end 55 of the inner shaft 54 of the insertion instrument 52 is inserted into the proximal socket 28 of the facet screw 10. The control 60 of the insertion instrument 52 is rotated in a first direction to rotate the outer shaft 56 to thread the inner threads (not shown) of the outer shaft 56 onto the outer threads 26 of the head 18 of the facet screw 10. After the facet screw 10 is connected to the distal end of the insertion instrument 52, the handle 58 is connected to the inner shaft 54. Then, the facet screw 10 and connected insertion instrument 52 is placed over the guide wire 76 and delivered through the lumen of the second dilator 94 into the patient as seen in FIG. 21. When the distal end of the facet screw 10 reaches the starting point 112, the handle 58 is rotated in one direction to begin threading the facet screw 10 into the vertebral body. The handle 58 is rotated and the facet screw 10 is threaded into the inferior articular process 114 and through the inferior articular surface associated with superior vertebra L3. The facet screw 10 is further driven across the target facet joint 110 into the superior articular surface associated with the lower vertebra L5 and into the pedicle of the lower vertebra L5. As the facet screw 10 is driven the seating surface 32 of the screw head 18 contacts vertebra at the starting point 112 as shown in FIGS. 22 and 23 preventing further driving of the facet screw 10. The trajectory 118 is shown marked with an arrow in FIG. 22. Once the facet screw 10 is seated, the control 60 of the insertion instrument 52 is rotated in a second direction to unthread the inner threads of the distal outer shaft 56 from the outer threads 26 of the screw head 18 to disconnect the insertion instrument 52 from the facet screw 10. The insertion instrument 52, second dilator 94 and guide wire 76 are removed from the patient and the incision is sutured and closed. The guide wire 76 is not removed until at least a portion of the screw 10 is seated within the vertebra. If needed, the facet screw 10 can be easily removed and recovered from the patient by attaching the insertion instrument 52 to the head 18 of the facet screw 10 and turning the handle 58 in the opposite direction to drive the screw 10 out of the bone.

The procedure is repeated for implanting a second facet screw 10 in the facet joint on the other side of the spine resulting in a second incision contralateral to the new target facet joint for bilateral facet screw fixation. Advantageously, only two small stab incisions result and they are located on both sides of the midline.

Numerous advantages are gained by the surgical method and use of the facet screw 10 of the present invention. The present invention requires less operative time for the subject and thus decreasing blood loss experienced in longer surgical procedures. The incision required to accomplish the present invention is minimal. Also, the operative time and the amount of fluoroscopy are reduced with a trajectory that crosses the interspinous ligament and employs the spinous processes as guideposts and anatomical landmarks. There is a decreased cost because for a single level fusion only two facet screws of the present invention are required when compared to a pedicle screw system that would require four screws and two rods. Furthermore, the system is less invasive and bulky and provides comparable stiffness and rigidity as a pedicle screw system While the description of the facet screw 10 and insertion instrument 52 is described in relation to spinal surgery, it should be understood that the system will find use in other areas of surgery in which a surgeon wishes to implant a screw to connect two pieces of bone.

Although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above.

We claim:

1. A surgical method for implanting a facet screw into a spine of a patient comprising the steps of:
    identifying a target facet joint located on a first side of a midline of a patient's spine; the target facet joint comprising the inferior articular face of a first vertebral body and the superior articular face of an adjacent lower second vertebral body;
    inserting a facet screw into a patient at a point of skin penetration located on a second side of the midline of the patient's spine that is opposite from the first side of the midline and cephalad of the target facet joint;
    moving the facet screw subcutaneously from the point of skin penetration through an interspinous ligament located between the first vertebral body and adjacent higher third vertebral body at a point of interspinous ligament penetration;
    moving the facet screw subcutaneously from the point of interspinous ligament penetration to the first vertebral body at a location adjacent to the target facet joint on the first side of the midline;
    delivering the facet screw into the bone of the first vertebral body at a location adjacent to the target facet joint; and
    driving the facet screw across the upper and lower articular faces of the target facet joint.

2. The surgical method of claim 1 further including the steps of:
    inserting a target needle comprising a trocar portion and a cannula portion into a patient at a point of skin penetration;
    moving the distal end of the target needle subcutaneously from the point of skin penetration through an interspinous ligament located between the first vertebral body and the adjacent higher third vertebral body creating a point of interspinous ligament penetration;
    moving the distal end of the target needle to contact the first vertebral body at a location adjacent to the target facet joint;
    docking the target needle into the first vertebral body at a location adjacent to the target facet joint;
    removing the trocar portion of the target needle;

inserting a guide wire into the cannula portion of the target needle;

docking the guide wire into the first vertebral body at a location adjacent to the target facet joint;

attaching the facet screw to the distal end of an insertion instrument; and passing the facet screw and insertion instrument over the guide wire to the first vertebral body.

3. The surgical method of claim 2 wherein the step of delivering the facet screw into the bone of the first vertebral body includes rotating the insertion instrument to self-tap the facet screw.

4. The surgical method of claim 1 wherein the step of driving the facet screw includes driving until a seating flange formed on the facet screw contacts the first vertebral body.

5. The surgical method of claim 1 wherein the step of inserting a facet screw includes the step of inserting a facet screw having a head portion, threaded portion distal to the head portion and a threadless portion distal to the threaded portion, and a longitudinally extending flute formed in the facet screw; the flute having a radial cutting face and heel face interconnected with the cutting face at one end and intersecting with the outer surface at heel edge; wherein the heel edge is curved and the flute interrupts a portion of the threaded portion.

6. The surgical method of claim 1 further including the step of creating a point of skin penetration.

7. The surgical method of claim 6 wherein the step of creating a point of skin penetration includes creating a stab incision, a percutaneous incision, a minimally invasive incision, a mini-open incision or open incision.

8. The surgical method of claim 1 wherein the step of moving the facet screw subcutaneously from the point of skin penetration through an interspinous ligament includes contacting a spinous process of the third vertebral body.

9. The surgical method of claim 1 wherein the step of moving the facet screw through the interspinous ligament includes contacting the spinous process of the first vertebral body.

10. The surgical method of claim 2 further including the steps of:

delivering a first dilator over the guide wire to the first vertebral body;

delivering a second dilator over the first dilator and guide wire to the first vertebral body;

removing the first dilator after delivering the second dilator;

wherein the step of passing the facet screw and insertion instrument over the guide wire includes delivering the facet screw and insertion instrument into the second dilator.

11. A surgical method for implanting a facet screw across a target facet joint comprising a first vertebral body and a second vertebral body in a minimally invasive surgical procedure comprising the steps of:

delivering the facet screw through a skin incision contralateral to the target facet joint;

passing the facet screw through the interspinous ligament to a location on the first vertebral body adjacent to the target facet joint; and driving the facet screw into the first vertebral body;

using the spinous process of the first vertebral body and the spinous process of an adjacent higher third vertebral body as guideposts; and fixing the target facet joint with the facet screw.

* * * * *